United States Patent [19]

Schober et al.

[11] 4,373,751
[45] Feb. 15, 1983

[54] EXHAUST ADAPTER FOR EXHAUST GAS MEASUREMENTS

[75] Inventors: Karl Schober, Weinstadt; Fritz Groll, Fellbach, both of Fed. Rep. of Germany

[73] Assignee: Daimler-Benz Aktiengesellschaft, Stuttgart, Fed. Rep. of Germany

[21] Appl. No.: 150,097

[22] Filed: May 15, 1980

[30] Foreign Application Priority Data

May 26, 1979 [DE] Fed. Rep. of Germany ....... 2921417

[51] Int. Cl.³ .............................................. F16L 39/00
[52] U.S. Cl. ................................ 285/137 R; 285/337; 285/180; 285/420
[58] Field of Search ............... 73/23; 285/137 R, 337, 285/125, 126, 180, 421, 420, 346

[56] References Cited

U.S. PATENT DOCUMENTS

| 683,287 | 9/1901 | Hutchinson | 285/126 |
|---|---|---|---|
| 766,754 | 8/1904 | Carlson | 285/420 X |
| 1,685,459 | 9/1928 | MacClatchie | 285/332 X |
| 1,852,279 | 4/1932 | Armacost et al. | 285/137 R |
| 1,958,906 | 5/1934 | Ard | 285/125 |
| 1,962,401 | 6/1934 | McWane | 285/337 X |
| 2,798,745 | 7/1957 | Nelson | 285/137 R X |
| 4,160,373 | 7/1979 | Fastaia et al. | 73/23 |

FOREIGN PATENT DOCUMENTS

| 1005793 | 4/1957 | Fed. Rep. of Germany ... 285/137 R |
| 718275 | 11/1954 | United Kingdom ................ 285/337 |
| 957909 | 5/1964 | United Kingdom ........... 285/137 R |

Primary Examiner—Thomas F. Callaghan
Attorney, Agent, or Firm—Paul M. Craig, Jr.

[57] ABSTRACT

An exhaust adapter for exhaust gas measurements which can be attached to the tail pipe of an exhaust unit and to which can be connected a hose leading to the analyzing measuring system. Two pipes, one telescoped into the other, are provided for attachment to a tail pipe. An elastic sealing ring is arranged between the end edge of the inner pipe and a drawn-in collar of the outer pipe. The outer pipe may be restrained with respect to the inner pipe for a gastight seal on the tail pipe by the measure of a compression of the sealing ring.

4 Claims, 3 Drawing Figures

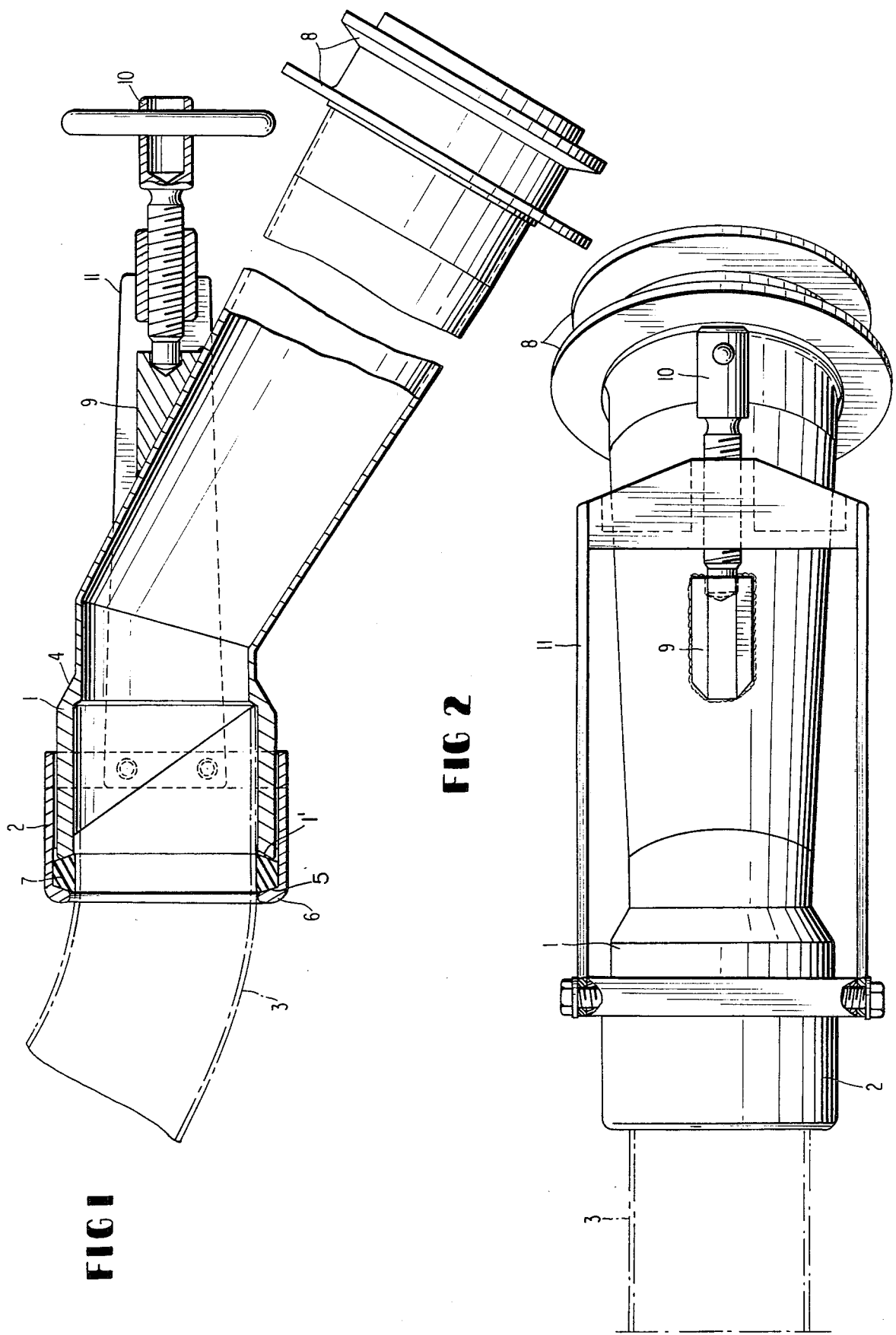

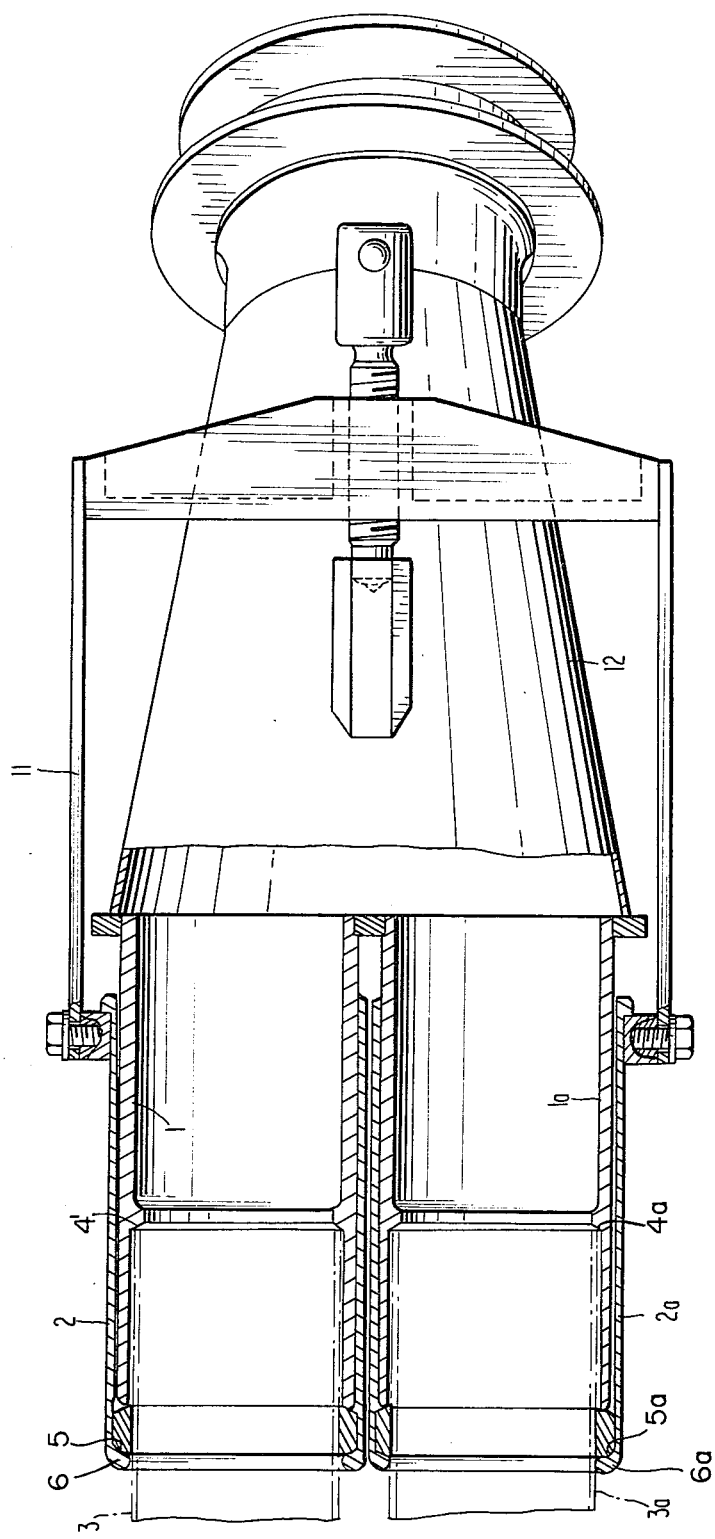

EXHAUST ADAPTER FOR EXHAUST GAS MEASUREMENTS

The present invention relates to an adapter and, more particularly, to an adapter for enabling a connecting of an exhaust unit to an exhaust gas measuring and/or analyzing unit.

In order to analyze deleterious substances in, for example, automobile exhaust gases, it is necessary to connect an exhaust unit of the automobile, used for traversing power curves on a roller-type test stand, to a measuring or analyzing system by means of an adapter and a metallic conduit.

The aim underlying the present invention essentially resides in providing an adapter which is attachable to a tail pipe of an exhaust unit and to which may be connected a hose leading to a measuring and/or analyzing system, with the adapter being constructed so that it can be mounted quickly and in a gas tight fashion and so that tolerances in an outer diameter of the tail pipe will have no effect on a secure mounting of the adapter to the exhaust unit.

In accordance with advantageous features of the present invention, two pipes are provided one of which is telescoped into the other with the two pipes being adapted to be attached to a tail pipe of the exhaust unit. An elastic sealing ring is arranged between an end edge of the inner pipe and a drawn-in collar of the outer pipe with the outer pipe being restrainable with respect to the inner pipe for a gastight seat on the tail pipe by virtue of a compressing of the elastic sealing ring.

By restraining the outer pipe with respect to the inner pipe, a sealing ring is firmly pressed against the tail pipe of the exhaust unit so that the adapter is firmly seated on the tail pipe and exhaust gases cannot escape at the junction zone. Moreover, any differences in tolerances in the dimensions of the tail pipes are compensated for by a more or less strong compression of the sealing ring.

In order to securely urge the sealing ring against a tail pipe, in accordance with further advantageous features of the present invention, an end edge of the inner pipe is provided with a bevel and an inner collar surface of the outer pipe is also beveled in such a way that the compressed sealing ring assumes a trapezoidal cross sectional configuration.

In order to restrain the pipes with respect to each other, in accordance with a further advantageous feature of the present invention, a clamping bracket is connected to the outer pipe with the bracket having a clamping screw which rests, during the restraining step, on the inner pipe.

In order to limit the extent to which the device is pushed onto the tail pipe, it is also possible in accordance with the present invention, to provide a stop collar in the interior of the inner pipe which stop collar functions to limit the insertion depth of the tail pipe of the exhaust unit.

The inner pipe, after the stop collar, may, in accordance with the present invention, be inherently bent and the clamping screw may lie in an extension of the longitudinal axis of symmetry of the portion of the inner pipe pushed into the outer pipe. By this arrangement, a relatively easy manipulation of the adapter is possible and the restraining takes place exactly in the axial direction.

In accordance with the present invention, an adapter may be provided for connection to two tail pipes of an exhaust unit which lie in parallel side by side relation. In this situation, the clamping bracket with the clamping screw engages suitably respectively one outer pipe and the inner pipes are combined with a funnel-like connector into a common inner pipe.

Accordingly, it is an object of the present invention to provide an adapter for enabling the connecting of an exhaust unit to an exhaust gas measuring and/or analyzing unit which avoids, by simple means, shortcomings and disadvantages encountered in the prior art.

Another object of the present invention resides in providing an adapter for enabling a connecting of an exhaust unit to an exhaust gas measuring and/or analyzing unit which may be quickly mounted to the exhaust unit.

Yet another object of the present invention resides in providing an adapter for enabling a connecting of an exhaust unit to an exhaust gas measuring and/or analyzing unit which ensures a gastight connection at an exhaust pipe of the exhaust unit.

A further object of the present invention resides in providing an adapter for enabling a connecting of an exhaust unit to an exhaust gas measuring and/or analyzing unit which is simple in construction and therefore relatively inexpensive to manufacture.

These and other objects, features, and advantages of the present invention will become more apparent from the following description when taken in connection with the accompanying drawings which show, for the purposes of illustration only, two embodiments in accordance with the present invention, and wherein:

FIG. 1 is a partially schematic longitudinal cross sectional view of an exhaust adapter in accordance with the present invention for an exhaust unit with a tail pipe;

FIG. 2 is a top view of the exhaust adapter of FIG. 1; and

FIG. 3 is a partially schematic longitudinal cross sectional view of another embodiment of an exhaust adapter in accordance with the present invention for an exhaust unit with two tail pipes.

Referring now to the drawings wherein like reference numerals are used in both views to designate like parts and, more particularly, to FIGS. 1 and 2, according to these figures, an exhaust adapter for connecting a tail pipe to an exhaust gas measuring and/or analyzing unit essentially includes an inner pipe 1 and an outer pipe 2 pushed onto the inner pipe 1 with both the inner and outer pipes 1, 2 being attached onto a tail pipe 3 of an exhaust unit to such an extent that an end of the tail pipe 3 abuts a stop collar 4 provided in the interior of the inner pipe 1.

An end edge 1' of the inner pipe 1 and an inner collar surface 5 of a drawn-in collar 6 at the outer pipe 2 are beveled in such a way that an elastic sealing ring 7 of rectangular cross section, arranged between an end face of the inner pipe and the drawn-in collar 6, assumes, as shown most clearly in FIG. 1, a trapezoidal cross section when the adapter is mounted onto the tail pipe 3.

In an area following the stop collar 4, the inner pipe 1 is bent and, at an end portion thereof, provided with flanges 8 for connecting a metallic hose leading to a measuring and/or analyzing system (not shown). In an extension of the longitudinal axis of symmetry through a portion of the inner pipe 1 which is pushed onto the tail pipe 3, a supporting lug 9 is provided on the inner pipe 1 in an area of the bend. A clamping screw 10 and clamping bracket 11 connected to the screw are supported on the lug 9. The clamping bracket 11, as shown most clearly in FIG. 2, is articulated to the end of the outer pipe 2.

With the clamping screw not yet tightened, the sealing ring 7 assumes a rectangular initial cross section. To attach the exhaust adapter to a tail pipe, the inner pipe 1 is placed with the outer pipe 2 onto the tail pipe 3. Thereupon, the clamping screw 10 is tightened so that the outer pipe 2 moves in a direction toward the inner pipe 1 with the sealing ring 7 being compressed and urged in a direction toward the tail pipe 3. By a compression of the sealing ring 7, a secure and gastight mounting of the exhaust adapter at the tail pipe 3 is readily obtained.

For exhaust units having two tail pipes 3, 3a, as shown in FIG. 3, the outer pipes 2, 2a are pushed onto the inner pipes 1, 1a with both of the inner and outer pipes 1, 1a, 2, 2a being respectively attached onto tail pipes 3, 3a of the exhaust unit to such an extent that the tail pipe 3 abuts a stop collar 4' and the tail pipe 3a abuts a stop collar 4a respectively provided in the interior of the inner pipes 1, 1a.

An end edge 1', 1'' of the inner pipes 1, 1a and an inner collar surface 5, 5a of the drawn-in collar 6 or 6a, as with the exhaust adapter of FIGS. 1 and 2 are beveled in such a way that an elastic sealing ring 7 of rectangular cross section, arranged between an end face of the inner pipe 1, 1a and drawn-in collar 6 or 6a assumes a trapezoidal cross section when the adapter is mounted to the tail pipes 3, 3a. Thus, as compared with the exhaust adapter of FIGS. 1 and 2, the exhaust adapter of FIG. 3 provides a duplicate parallel arrangement.

The two inner pipes 1, 1a are combined by means of a funnel-shaped member 12 with the clamping bracket 11 engaging the outer pipes 2, 2a with respective ends thereof. In all other respects the structure and function of the exhaust adapter of FIG. 3 corresponds to that of the exhaust adapter of FIGS. 1 and 2.

While we have shown and described only two embodiments in accordance with the present invention, it is understood that the same is not limited thereto but is susceptible of numerous changes and modifications as known to one having ordinary skill in the art, and We therefore do not wish to be limited to the details shown and described herein, but intend to cover all such modifications as are encompassed by the scope of the appended claims.

We claim:

1. An exhaust adapter for enabling exhaust gas measurement, the exhaust adapter being adapted to be attached to an exhaust unit and adapted to be connected to a hose leading to an exhaust gas analyzing measuring system, the exhaust unit includes two tailpipes disposed in a side by side parallel relationship, characterized in that the exhaust adapter includes at least one outer pipe and at least one inner pipe telescopically accommodated therein, the outer and inner pipes are adapted to accommodate at least a portion of the respective tailpipes, a sealing ring is disposed between an end edge of the respective inner pipes and a collar of an associated outer pipe, a funnel shaped member is provided for combining free ends of the two inner pipes, and in that means are provided for restraining each outer pipe with respect to an associated inner pipe and for compressing the respective sealing ring so as to provide for a gastight seal of the adapter on the respective tail pipes comprising a clamping bracket having one end thereof connected to one of the outer pipes and the other end thereof connected to the other outer pipe, and a second means cooperable with the clamping bracket for restraining the respective outer pipes with respect to the associated inner pipes, the second means being adapted to rest on the funnel shaped member when the respective outer pipes are restrained with respect to the associated inner pipes.

2. An exhaust adapter according to claim 1, characterized in that each collar of the outer pipes includes a surface engageable with the sealing ring, and in that the surfaces of the respective collars and the end edge of the respective inner pipes are beveled such that the compressed sealing ring has a trapezoidal cross sectional configuration when the adapter is mounted on the respective tail pipes.

3. An exhaust adapter according to one of claims 1 or 2, characterized in that means are provided for limiting an insertion depth of the tail pipe into the respective inner pipes.

4. An exhaust adapter according to claim 3, characterized in that the limiting means is a stop collar arranged in an interior of each of the inner pipes.

* * * * *